United States Patent [19]

Tabata et al.

[11] Patent Number: 5,432,009

[45] Date of Patent: Jul. 11, 1995

[54] FILM FOR FIRST-AID STICKING PLASTER

[75] Inventors: Hironori Tabata, Ibaraki; Masao Ogasa, Takatsuki; Kiyomi Uenomachi, Kusatsu; Hideshi Matsumoto, Kyoto, all of Japan

[73] Assignee: Sekisui Kagaku Kogyo Kabushiki Kaisha, Osaka, Japan

[21] Appl. No.: 261,116

[22] Filed: Jun. 14, 1994

[51] Int. Cl.⁶ .................. C08L 23/14; C08F 297/08
[52] U.S. Cl. .................. 428/516; 525/247; 525/319; 525/322; 525/323; 526/348.1; 602/904
[58] Field of Search .......... 525/319, 322, 323; 526/348.1; 428/516

[56] References Cited

U.S. PATENT DOCUMENTS

| | | | |
|---|---|---|---|
| 5,212,246 | 5/1993 | Ogale | 525/323 X |
| 5,286,552 | 2/1994 | Lesca et al. | 525/323 X |
| 5,302,454 | 4/1994 | Cecchin et al. | 525/323 X |
| 5,324,784 | 6/1994 | Fujita et al. | 525/323 X |
| 5,332,789 | 7/1994 | Tanaka et al. | 525/323 |

FOREIGN PATENT DOCUMENTS

| | | |
|---|---|---|
| 0400333 | 4/1990 | European Pat. Off. |
| 0492942 | 12/1991 | European Pat. Off. |
| 0515855 | 4/1992 | European Pat. Off. |
| 3937941 | 11/1989 | Germany . |
| 59199628 | 11/1984 | Japan . |
| 1223185 | 9/1989 | Japan . |
| 2001284 | 1/1990 | Japan . |

*Primary Examiner*—Fred Teskin
*Attorney, Agent, or Firm*—Townsend & Banta

[57] ABSTRACT

A film for a first-aid sticking plaster consisting of polypropylene resin having a weight average molecular weight within a range of 80,000 to 500,000, with resin elution quantities according to cross fractionation chromatograph in ranges of 45 to 80 percent by weight at 0° to 10° C., 5 to 35 percent by weight at 10° to 70° C., 1 to 30 percent by weight at 70° to 95° C., and 5 to 35 percent by weight at 95° to 125° C.

20 Claims, 2 Drawing Sheets

FILM FOR FIRST-AID STICKING PLASTER

BACKGROUND OF THE INVENTION

1. Field of the Invention

The present invention relates to a film for a first-aid sticking plaster, and more particularly, it relates to a film for a first-aid sticking plaster which can obtain a flexible first-aid sticking plaster having excellent feeling, with a low possibility of compressing the affected part.

2. Description of the Background Art

In general, a sticking plaster, particularly a first-aid sticking plaster is prepared through the following steps: First, a soft film is prepared so that its surface is coated with an adhesive, and a gauze or the like is attached onto the adhesive. Further, a separator is disposed on a gauze to obtain a layered product. Then, the layered product is punched into prescribed dimensions, and packing papers are superposed on front and back surfaces of the punched layered product and cut into prescribed dimensions, to obtain a first-aid sticking plaster.

The soft film employed for the aforementioned first-aid sticking plaster is generally made of a material which is mainly composed of plasticized polyvinyl chloride (hereinafter referred to as plasticized PVC) prepared by calendering or sol casting, in consideration of flexibility, stretchability and feeling.

However, a plasticized PVC film contains a plasticizer in a large amount. Thus, the plasticizer may be transferred from the film toward the adhesive to reduce its adhesion or adhesive strength between the film and the adhesive, leading to separation of the sticking plaster. Further, problems in employment of plasticized PVC, which is a polymer containing chlorine, are recently discussed in all fields in consideration of environment.

To this end, positive development is now being made on polyolefin resin having flexibility and high stretchability, as a material for taking place of the plasticized PVC.

A film of such polyolefin resin is prepared from polyethylene, an ethylene-vinyl acetate copolymer, polybutadiene or an ethylene-propylene copolymer, for example. Japanese Patent Publication No. 57-11342 (1982) discloses a Film for a first-aid sticking plaster which is prepared by drawing a polyolefin composition consisting of at least one of an ethylene-α-olefin copolymer, LDPE (low density polyethylene) and PP (polypropylene) by 1.5 to 3.5 times, while Japanese Patent Laying-Open No. 62-82967 (1987) discloses a film consisting of a hydrocarbon elastomer such as ethylene-propylene rubber or an ethylene-propylene-diene ternary copolymer and a polyolefin compound such as an ethylene-vinyl acetate copolymer.

However, such a film of polyolefin resin is insufficient in stretchability and stress relaxation in application, which are required for a first-aid sticking plaster. Namely, the film is so insufficient in stretchability that the first-aid sticking plaster may be loosened immediately after application. Further, the film is so insufficient in stress relaxation that the first-aid sticking plaster compresses the affected part upon application or is separated immediately after application. Thus, the film is not necessarily suitable for actual use.

SUMMARY OF THE INVENTION

In order to solve the aforementioned problems of the conventional film for a first-aid sticking plaster employing polyolefin resin, an object of the present invention is to provide a film for a first-aid sticking plaster substantially containing no plasticizer and having excellent flexibility, stretchability and feeling, which can reduce compression on the affected part with quick stress relaxation upon extension by employing specific polypropylene resin.

The inventors have made deep study for attaining the aforementioned object, to find that it is possible to solve the aforementioned various problems by preparing resin for a film for a first-aid sticking plaster from polypropylene resin having a specific weight average molecular weight and exhibiting an elution quantity of a constant range at a specific temperature.

According to the present invention, provided is a film for a first-aid sticking plaster consisting of polypropylene resin having a weight average molecular weight within a range of 80,000 to 500,000, with resin elution quantities within ranges of 45 to 80 percent by weight at 0° to 10° C., 5 to 35 percent by weight at 10 to 70° C., 1 to 30 percent by weight at 70 to 95° C. and 5 to 35 percent by weight at 95° to 125° C. in the total polypropylene resin quantity according to cross fractionation chromatograph.

According to the present invention, the polypropylene resin has a weight average molecular weight of 80,000 to 500,000, preferably 80,000 to 450,000, and more preferably 100,000 to 400,000 in measurement through high temperature type gel permeation chromatography (GPC) (150 CV) by Milipore Corporation Waters Chromatography Division. The film is inferior in stretchability and strength if the weight average molecular weight is less than 80,000, while no sufficient flexibility can be attained if the weight average molecular weight exceeds 500,000.

The cross fractionation chromatograph employed in the present invention is as follows:

Polypropylene resin was first dissolved in o-dichlorobenzene at a temperature for completely dissolving the polypropylene resin, and a sample solution (0.4 percent by weight in concentration) of 140° C. was collected by 0.5 ml and set in a TREF column. Then, this solution was reduced in temperature to 0° C. under a constant condition of 1° C/min., and held for 30minutes. Then, components thereof were successively eluted from the lower temperature side at a flow rate of 1.0 ml, and taken out into an SEC column (140° C.). This method is called temperature rising elution fractionation. The respective eluted components were subjected to measurement of weight average molecular weights in an SEC part, The column as employed was GPC AD-806MS (by Showa Denko K. K., with three serial columns of 8 mm in diameter and 250 mm in length).

Then, weight average molecular weights of the aforementioned respective components were measured by high temperature type GPC. The inventors employed a cross fractional chromatograph (CFC-T150A by Mitsubishi Petrochemical Co., Ltd.) comprising the aforementioned temperature rising elution fractionation (TREF) portion and a high temperature type GPC (SEC: size exclusion chromatograph) portion in its system, to carry out the aforementioned measurement.

According to the present invention, the polypropylene resin has a resin elution quantity of 45 to 80 percent by weight, preferably 50 to 75 percent by weight, in the total polypropylene resin quantity in a temperature range of at least 0° C. and not more than 10° C. according to the aforementioned cross fractionation chromatograph, The film as obtained has no flexibility if the elution quantity is less than 45 percent by weight in the aforementioned temperature range, while no sufficient strength is attained if the elution quantity exceeds 80 percent by weight.

The resin elution quantity at a temperature of 10° to 70° C., i.e., in a temperature range of at least 10° C. and not more than 70° C., is 5 to 35 percent by weight, preferably 5 to 30 percent by weight, in the total polypropylene resin quantity according to the aforementioned cross fractionation chromatograph. The film as obtained is inferior in flexibility if the elution quantity is less than 5 percent by weight in this temperature range, while the film is inferior in deformation recovery if the elution quantity exceeds 35 percent by weight.

The resin elution quantity in a temperature range of at least 70° C. and not more than 95° C. is 1 to 30 percent by weight, preferably 1 to 25 percent by weight, in the total propylene resin quantity according to the aforementioned cross fractionation chromatograph. The film is inferior in deformation recovery if the elution quantity is less than 1 percent by weight, while film strength is reduced if the elution quantity exceeds 30 percent by weight.

The resin elution quantity in a temperature range of at least 95° C. and not more than 125° C. is in a range of 5 to 35 percent by weight, preferably 5 to 30 percent by weight, in the total polypropylene resin quantity according to the aforementioned cross fractionation chromatograph. The film strength is inferior if the elution quantity is less than 5 percent by weight, while the film is inferior in flexibility if the elution quantity exceeds 35 percent by weight.

Weight average molecular weights of eluted resin in the aforementioned temperature ranges of 0° to 10° C., 10° to 70° C., 70° to 95° C. and 95° to 125° C. are preferably 100,000 to 300,000, 70,000 to 500,000, 50,000 to 500,000 and 50,000 to 500,000 respectively.

The film for a first-aid sticking plaster according to the present invention is preferably prepared from polypropylene resin having at least one fusion peak measured by a DSC (differential scanning calorimeter) between 130° C. and 170° C. with a total quantity of fusion heat of 5 to 40 mJ/mg at the peak. More preferably, the film has a thickness of 15 to 300 μm.

The polypropylene resin forming the inventive film preferably has at least one fusion peak in a temperature range of 130° C. to 170° C. by measurement with a DSC as described later. The film is reduced in heat resistance, strength and stretchability when the same has no fusion peak in this range.

Further, the total quantity of fusion heat is preferably in a range of 5 to 40 mJ/mg, and more preferably in a range of 7 to 35 mJ/mg. The film is reduced in heat resistance and strength if the quantity of fusion heat is less than 5 mJ/mg, while the crystal quantity of polypropylene is so increased that a problem may be caused in flexibility of the film or feeling on a human body portion such as a finger if the quantity of fusion heat exceeds 40 mJ/mg.

The polypropylene resin employed in the present invention is obtained by multistage polymerization including at least two stages. It is preferable to polymerize 5 to 35 percent by weight, more preferably 5 to 30 percent by weight, of a propylene homopolymer, a propylene-ethylene copolymer or a propylene-α-olefin copolymer in the first stage. Then, preferably 65 to 95 percent by weight, more preferably 70 to 95 percent by weight, of an ethylene-propylene copolymer elastomer is polymerized in the second or subsequent stage.

If the quantity of a propylene homopolymer, a propylene-ethylene copolymer or a propylene-α-olefin copolymer which is polymerized in the first stage is less than 5 percent by weight, the film as obtained is so extremely softened that its film strength is reduced. On the other hand, a problem is caused in flexibility of the film if the quantity exceeds 35 percent by weight.

Further, flexibility of the film is reduced if the quantity of an ethylene-propylene copolymer elastomer which is polymerized in the second or subsequent stage is less than 65 percent by weight, while film strength is reduced if the quantity exceeds 95 percent by weight.

In the aforementioned propylene-ethylene copolymer or propylene-α-olefin copolymer, the content of ethylene or α-olefin is preferably not more than 10 percent by weight with respect to propylene.

On the other hand, the ethylene component of the ethylene-propylene copolymer elastomer is preferably contained within a range of 15 to 65 percent by weight, and more preferably 15 to 60 percent by weight. Such an ethylene-propylene copolymer elastomer is generally called ethylene-propylene rubber. The feature of the present invention resides in that this ethylene-propylene rubber is polymerized in the second or subsequent stage in multistage polymerization, so that the propylene homopolymer, the propylene-ethylene copolymer or the propylene-α-olefin copolymer polymerized in the first stage is mixed with the ethylene-propylene rubber at the molecular structure level (nano order). Thus, it is possible to obtain an olefin film which is extremely homogeneous and flexible.

According to the present invention, the α-olefin forming the copolymer can be prepared from that having a carbon number of at least 4, such as 1-butene, 1-pentene, 1-hexene, 1-heptene or 1-octene, for example.

The inventive film for a first-aid sticking plaster preferably has not a clear yield point, while stress residual rates after 5 and 300 seconds from extension by 10% are not more than 80% and 60% respectively. More preferably, relations of $F(30) > F(10) > F(5)$ and $0.2$ kgf $< F(30) \leqq 1.2$ kgf, $0.2$ kgf $\leqq F(10) \leqq 0.8$ kgf, and $0.1$ kgf $\leqq F(5) \leqq 0.6$ kgf hold assuming that $F(x)$ represents tensile strength of a film having a width of 19 mm in extension by x %.

If the tensile strength $F(x)$ in extension by x % does not satisfy $F(30) > F(10) > F(5)$, a sticking plaster formed by the inventive film may be stretched beyond necessity in application. This may lead to such problems that (1) a gauze portion deviates from the affected part, and (2) it is difficult to apply the sticking plaster.

If $F(50) \leqq 0.2$ kgf, $F(10) < 0.2$ kgf and $F(5) < 0.1$ kgf, the sticking plaster is stretched beyond necessity in application or upon movement of a finger or the like after application. This leads to such problems that (1) it may be difficult to apply the sticking plaster, and (2) the sticking plaster may be loosened after application. If $F(30) > 1.2$ kgf, $F(10) > 0.8$ kgf and $F(5) > 0.6$ kgf, tensile strength is so strong that no sufficient extension is attained in and after application. This leads to such problems that (1) the sticking plaster is inferior in feeling, (2) the sticking plaster is hard to apply (unfittable to the skin in this case), and (3) strong resistance is caused against movement of a finger or the like.

The inventive film for a first-aid sticking plaster has relations of $R(10, 5) \leq 80\%$ and $R(10,300) \leq 60\%$ assuming that $R(10, y)$ % represents a stress residual rate upon a lapse of y seconds after extension by 10%.

If the stress residual rate $R(10, y)$ is $R(10, 5) > 80\%$, this leads to excessive tightness immediately after application. If $R(10,300) > 60\%$, on the other hand, this leads to excessive compression after application.

The inventive film for a first-aid sticking plaster preferably has a thickness of 30 to 200 $\mu$m, more preferably 50 to 90 $\mu$m. If the thickness is smaller than 30 $\mu$m, the sticking plaster is so reduced in nerve that the same is easily creased in application. If the thickness exceeds 200 $\mu$m, on the other hand, the sticking plaster is so inferior in flexibility that it is difficult to wind the same on a thin portion such as a finger.

The polypropylene resin for forming the inventive film is prepared by the following multistage polymerization, for example: In a first stage, polymerization is carried out with a propylene monomer and an $\alpha$-olefin monomer other than propylene at need under presence of a titanium compound catalyst and an aluminum compound catalyst, to obtain first propylene polyolefin. This polyolefin can be a propylene homopolymer, a propylene-ethylene copolymer or a propylene-$\alpha$-olefin copolymer. In a second stage, the propylene polyolefin containing titanium is copolymerized with an olefin monomer (ethylene or propylene) under presence of the aforementioned titanium compound and aluminum compound catalysts, to obtain second polyolefin. Thereafter a multistage copolymerization reaction can be similarly made in response to the object.

Some methods have already been proposed in relation to preparation of such polypropylene resin. For example, Japanese Patent Laying-Open No. 4-224809 (1992) describes a method of employing a spherical Ti catalyst having a mean particle size of 5 $\mu$m, which is prepared by copulverizing titanium trichloride and magnesium chloride and treating the same with n-butyl orthotitanate, 2-ethyl-1-hexanol, p-ethyl toluate, silicon trichloride, diisobutyl phthalate or the like, as a titanium compound and employing alkyl aluminum such as triethyl aluminum as an aluminum compound while adding a silicon compound, particularly diphenyldimethoxysilane as an electron donor in a polymerization vessel with further addition of ethyl iodide. The feature of this method resides in that the polymerization is not completed in a single stage but carried out in a multistage manner in two or more stages. Namely, it is possible to form a plurality of types of polymers in continuation during polymerization, whereby a copolymer of a blend type at a molecular level which is absolutely different from an ordinary polymer blend is formed by this method.

In conventional resin such as a block polypropylene copolymer, the content of a block portion which is copolymerized with propylene, i.e., a rubber component consisting of a propylene-ethylene or propylene-$\alpha$-olefin copolymer, is limited to about 50 percent by weight with respect to the original propylene quantity due to the process of preparing the same. Thus, it has been extremely difficult to implement flexibility such as that of plasticized PVC in polypropylene resin.

When the aforementioned polymerization blend is employed, however, it is possible to increase the content of the rubber component consisting of the copolymerized portion to about 80 to 95 percent by weight, thereby obtaining resin having physical properties which are similar to those of plasticized PVC. Thus, it is possible to prepare a blend compound which cannot be formed by an ordinary blending method with an extruder or the like in consideration of its viscosity. Methods of preparing such resin compositions are also described in Japanese Patent Laying-Open Nos. 4-96912 (1992), 4-96907 (1992), 3-174410 (1991), 2-170803 (1990), 2-170802 (1990), 61-42553 (1986) and 3-205439 (1991), in addition to the aforementioned gazette. Further, Japanese Patent Laying-Open No. 3-97747 (1991) discloses a method of first forming an adduct of magnesium chloride and alcohol as a titanium compound and thereafter treating the adduct with titanium trichloride and an electron donor. According to the present invention, the polypropylene resin can be prepared by any of these methods with no problem. Examples of resin obtained by any of the aforementioned methods are "PER" (trade name) by Tokuyama Soda Co., Ltd. and "Catalloy Pro-fax" (trade name) by Himont Inc..

The polypropylene film for a first-aid sticking plaster obtained in the aforementioned manner contains no plasticizer and has flexibility and stretchability with quick stress relaxation in extension. Thus, it is possible to obtain a first-aid sticking plaster having excellent feeling which will not compress the affected part by employing the inventive film as a material for forming such a sticking plaster.

The reason for this, which has not yet been clarified, is estimated as follows:

In the polypropylene resin employed in the present invention, amorphous polymers represented by the ethylene-propylene copolymer etc. which are introduced in a large quantity during polymerization are conceivably alloyed. Preparation of such resin may be enabled through employment of a titanium catalyst having extremely high activity and a long life. Some copolymers having different molecular structures exist in the polymer due to such polymerization, conceivably leading to morphology which is characterized in alloying of an ordinary resin part of polypropylene etc. and the copolymer parts. It is conceivable that the inventive film for a first-aid sticking plaster exhibits physical properties which are extremely similar to those of plasticized PVC as the result, although the same has no crosslinking in the resin.

According to a specific aspect of the present invention, another layer is also stacked in addition to the polypropylene resin layer. Such a layer is preferably prepared from a thermoplastic elastomer such as an olefin thermoplastic elastomer or a styrene thermoplastic elastomer. Such thermoplastic elastomers may be employed independently of or in combination with each other. The thermoplastic elastomer layer is adapted to adjust film strength (tensile strength in extension) without damaging flexibility and deformation recovery of the polypropylene resin layer, Examples of the olefin thermoplastic elastomer are ethylene-propylene rubber, ethylene-1-butene rubber, an ethylene-vinyl acetate copolymer and the like.

Examples of the styrene thermoplastic elastomer are a styrene-butadiene block copolymer, a styrene-isoprene block copolymer, a styrene-ethylene/butylene block copolymer, a styrene-ethylene/propylene block copolymer and the like.

According to a specific aspect of the present invention, at least one polypropylene resin layer and an olefin thermoplastic elastomer layer or a styrene thermoplastic elastomer layer are stacked with each other. Alternatively, at least one polypropylene resin layer may be stacked with an olefin thermoplastic elastomer layer and a styrene thermoplastic elastomer layer for forming the inventive film for a first-aid sticking plaster.

The polypropylene resin layer is preferably at a ratio in thickness of 1/1 to 10/1 to the other resin layer. If the ratio is out of the aforementioned range, the first-aid sticking plaster prepared from the inventive film cannot attain preferable properties such as tensile strength and stress relaxation.

The inventive film for a first-aid sticking plaster is preferably drawn at least in a single direction, for maintaining flexibility, stretchability and stress relaxation in extension and attaining sufficient tensile strength so that the sticking plaster is not excessively stretched even if the same is strongly pulled in application or re-application thereof.

The film is drawn at a temperature of 75° to 150° C. The film is irregularly drawn if the drawing temperature is less than 75° C. while sufficient tensile strength cannot be attained if the drawing temperature exceeds 150° C.

Further, the film is drawn at a magnification of 1.1 to 4 times, preferably 1.2 to 3 times. If the film is drawn in excess of 4 times, stress strongly results from such drawing to cause excessive heat contraction. If the magnification is less than 1.1 times, on the other hand, sufficient tensile stress cannot be attained.

The inventive film for a first-aid sticking plaster may be annealed after the aforementioned drawing, so that the film is heat treated after the drawing, relieved from stress caused by the drawing and suppressed from heat contraction. This annealing is preferably carried out at a temperature of 80° to 160° C. If the annealing temperature is less than 80° C., excessive heat contraction is caused since stress resulting from drawing cannot be sufficiently relaxed. If the annealing temperature exceeds 160° C., on the other hand, the film is extremely softened.

The film may be drawn by any method such as tenter drawing, vertical uniaxial orientation, simultaneous biaxial orientation, sequential biaxial orientation, roll drawing, tubular drawing or the like, so far as the same can be uniformly drawn at least in one direction.

In the present invention another olefin resin may be blended in or layered on the polypropylene resin layer without departing from the spirit or purpose of the invention. As the olefin resin there may be used low density polyethylene, linear low density polyethylene, very low density polyethylene, polyethylene obtained by using metallocene catalyst, high density polyethylene, propylene-ethylene copolymer, propylene monopolymer, propylene-α olefin copolymer of the like.

According to the present invention, it is possible to add a stabilizer such as an antioxidant or an ultraviolet ray absorber, a filler such as precipitated barium sulfate, talc, calcium carbonate, mica or titanium oxide, a coloring agent and the like to each resin layer.

A layered type film for a first-aid sticking plaster can be obtained by independently molding each resin into a prescribed thickness by an ordinary T-die method, inflation or calendering and thereafter carrying out lamination, or coextruding the resin materials into prescribed thicknesses.

This film may be transparent with no color, transparent with a color, or opaque with a color.

The film for a first-aid sticking plaster as obtained is employed as a base material for forming a first-aid sticking plaster. An exemplary method of forming such a first-aid sticking plaster is now described.

First, one surface of the inventive film for a first-aid sticking plaster is subjected to corona treatment or anchor coating at need, and thereafter provided with an adhesive layer, so that a gauze or the like is stacked thereon and a separator is disposed thereon. Then, the layered product as obtained is punched into prescribed dimensions, and packing papers are superposed on front and back surfaces of the punched layered product and cut into prescribed dimensions, to obtain a first-aid sticking plaster. When the aforementioned corona treatment is carried out, the film preferably has surface tension of at least about 38 dyn/cm.

The adhesive layer may be provided on the overall surface of the base material film, or may be freely set in the form of fine lines, a lattice, dispersed dots or a surface provided with a number of small circles coated with no adhesive, in response to its usage.

The adhesive layer is not particularly restricted in material but can be prepared from a proper adhesive such as natural rubber, synthetic rubber, an acrylic adhesive, a urethane adhesive, a vinyl ether adhesive or a silicone adhesive in any form of a solvent, an emulsion type adhesive or a hot-melt adhesive.

A method of applying the adhesive onto the base material film is not restricted in particular. The adhesive may be directly applied onto the film surface, or may be applied to a relase paper or film so that the separator is superposed with the base material film to transfer the adhesive to the film.

A surface of the base material film may be subjected to printing in an arbitrary shape and dimensions, in response to the object. For example, a mesh, dispersed dots or a character for children can be printed on this surface.

The first-aid sticking plaster obtained by using the inventive film can provide a flexible sticking plaster having stretchability with excellent feeling, which will not compress the affected part.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
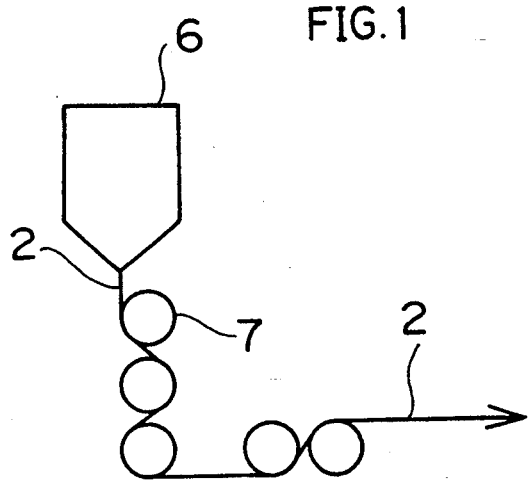
FIG. 1 is a flow sheet showing an exemplary method of preparing a film for a first-aid sticking plaster according to the present invention.

The present invention is now described in more concrete terms with reference to Examples, while the present invention is not restricted to these Examples.

In each of the Following Examples, a Fusion peak of polypropylene resin, a quantity of Fusion heat, contents of respective copolymer and ethylene, tensile strength, an extension recovery Factor, stress relaxation, heat contraction, and application Feeling for and applicability to a human body portion (Finger) were tested in the Following methods:

1. Fusion Peak of Polypropylene Resin and Quantity of Fusion Heat

About 10 mg of the inventive polypropylene resin was introduced into a platinum pan, and these values were measured with a SSC-5000 type DSC (differential scanning calorimeter) by Seiko Instruments & Electronics Ltd., Japan. In such measurement, each sample was once fused, thereafter cooled to −50° C. at a rate of 5° C./min., and then heated at a rate of 5° C./min 2. Contents of Copolymers and Ethylene The polypropylene resin was dissolved in o-dichlorobenzene at a temperature of 140° C. or that for completely dissolving the polypropylene resin, and then this solution was cooled at a constant cooling rate, to precipitate thin polymer layers on a surface of a previously prepared inactive carrier in order from that having the highest crystallinity and the largest weight average molecular weight. Then the precipitated polymer layers were continuously or stepwisely heated and successively eluted components were sampled to calculate contents of the respective copolymers. Further, low temperature eluted components were measured with $^1$H and $^{13}$C-NMR, to obtain an ethylene content from an integrated intensity ratio of a methyl group to a methylene group.

3. Tensile Strength

Samples were pulled by a tensile tester with a sample width of 19 mm or 20 mm, an initial sample length (length between grips) of 100 mm and a testing rate of 200 mm/min. to measure tensile strength at degrees of extension of 5% and 10%, with an additional degree of 30% in each of Examples 17 to 21 and with an additional degree of 50% in Examples 22 to 26.

4. Extension Recovery Factor

Bench marks were drawn at intervals of 50 mm on a strip-shaped sample of 19 mm or 20 mm in width, which in turn was pulled to a degree of extension of 50% by a tensile tester with an initial sample length of 100 mm and a testing rate of 200 mm/min. and immediately detached from the tester, to be subjected to measurement of bench mark intervals after 5 minutes, for calculation of permanent set (degree of extension). Assuming that this permanent set is Y %, an extension recovery factor (%) is obtained as follows:

$$\text{Extension Recovery Factor (\%)} = \frac{50 - Y}{50} \times 100$$

5. Stress Relaxation

Each sample was pulled by a tensile tester to 10% in ductility with a sample width of 19 mm or 20 mm, an initial sample length of 100 mm and a testing rate of 200 mm/min. and thereafter held in this state, so that time changes of tensile strength were measured after 5 seconds, 60 seconds and 300 seconds for calculating a stress residual rate as follows:

Stress Residual Rate (%) =

$$\frac{\text{Tensile Strength after lapse of Prescribed Time}}{\text{Initial Tensile Strength}} \times 100$$

6. Heat Contraction

Bench marks of 100 mm in length were drawn along machine and transverse directions of each film sample, which in turn was heated in a gear oven at 70° C. for 5 hours to be subjected to measurement of heat contraction values, and a larger value was employed.

$$\text{Heat Contraction (\%)} = \frac{100 - \text{Size after Heating}}{100} \times 100$$

7. Application Feeling for Human Body Portion (Finger)

A sticking plaster was wound on the second joint of a forefinger, which was bent and stretched for evaluating application feeling (pressure).

8. Applicability to Human Body Portion (Finger)

A sticking plaster was applied to the second joint of a forefinger, for evaluation of its crease and hardness.

EXAMPLE 1

Polypropylene resin ("PER (trade name) by Tokuyama Soda Co., Ltd., Japan) having a weight average molecular weight of 200,000 and elution quantities of 68.9 percent by weight at 0° to 10° C., 10.9 percent by weight at 10° to 70° C., 1.33 percent by weight at 70° to 95° C. and 18.9 percent by weight at 95° to 125° C. according to cross fractionation chromatograph was prepared. As shown in FIG. 1, this resin was extruded by a T-die 6 at a die temperature of about 240° C., to obtain a film 2 of 65 μm in thickness. Then, a surface 2a of the film 2 was corona-discharged, and thereafter the film was taken up to obtain a roll of the film 2 for a first-aid sticking plaster by winding the film 2 in the state that the surface 2a is inner side. Referring to FIG. 1, numeral 7 denotes a cooling roll.

As to the film 2 obtained in the aforementioned manner, tensile strength values in a machine direction (MD) and a transverse direction (TD), an extension recovery factor and stress relaxation were measured respectively. Table 1 shows the results.

Figure 2:
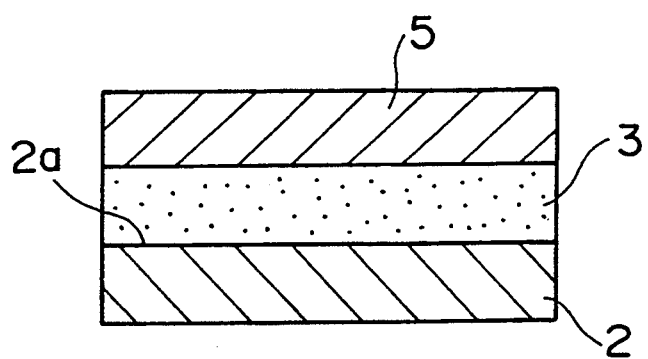
FIG. 2 is a sectional view showing the film for a first-aid sticking plaster and an adhesive layer, which is formed on a process paper, stacked thereon.

Then, a lubricated surface of a process paper 5 (see FIG. 2) prepared by stacking a polyethylene layer on both surfaces of a kraft paper and coating a surface of the polyethylene layer with a silicone release agent was coated with a rubber adhesive solution by a coater to attain a thickness of 40 μm after drying, thereby obtaining the process paper 5 having an adhesive layer 3. The rubber adhesive solution was prepared by a 35% toluene solution containing natural rubber, polyterpene resin, polybutene and an antioxidant. Then, the adhesive layer 3 supported by the process paper 5 was stacked on the corona-treated surface 2a of the film 2 and the laminate was taken up into the form of a roll by a winder in the state that the process paper 5 is outside.

Then, the roll-shaped laminate was cut into a width of 78 mm, thereby taking up an original tape A for a first-aid sticking plaster in the form of a roll.

Figure 3:
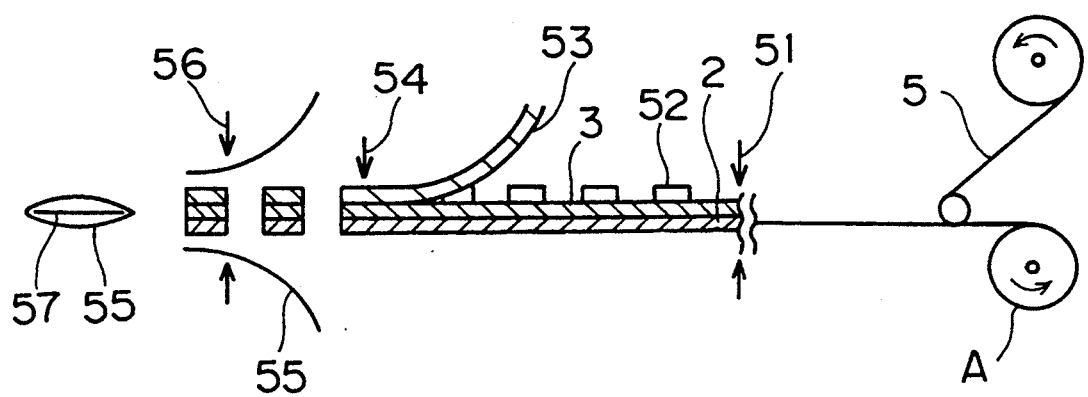
FIG. 3 schematically illustrates steps of preparing a first-aid sticking plaster.

As shown in FIG. 3, this original tape A for a first-aid sticking plaster was worked into a first-aid sticking plaster. The original tape A for a first-aid sticking plaster was delivered from the roll, and then the process paper 5 was separated from the film 2. Then, the film 2 and the adhesive layer 3 forming the original tape A were subjected to ordinary hole-forming 51 by a puncher. Then, a gauze 52 of 1 mm in thickness, 17 mm in width and 25 mm in length was supplied from a gauze supplier and attached onto an upper surface of the adhesive layer 3, and thereafter a surface-lubricated paper 53 was supplied from a surface-lubricated paper supplier and stacked on the adhesive layer 3 to cover an upper surface of the gauze 52.

Figure 4:
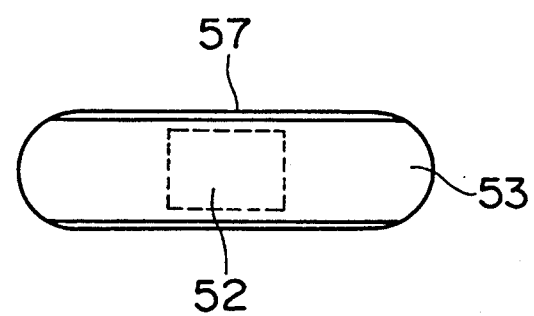
FIG. 4 is a plan view showing the first-aid sticking plaster.

Then, this laminate was punched as shown by an arrow 54 by another puncher into prescribed dimensions of 20 mm in width and 75 mm in length with arcuate ends of 12 mm in radius. Thereafter, packaging materials 55 and 55 were superposed on front and back surfaces of the punched substance as obtained, which in turn was cut as shown in an arrow 56 in FIG. 3 into each package for a first-aid sticking plaster 57 shown in FIG. 4.

This first-aid sticking plaster 57 was taken out from the package, separated from the surface-lubricated paper 53 and applied onto a forefinger, to be subjected to evaluation of application feeling in the aforementioned manner. Table 1 shows the results.

Example 2

Polypropylene resin ("Catalloy Pro-fax (trade name)" by Himont Inc. ) having a weight average molecular weight of 250,000 and elution quantities of 56.4 percent by weight at 0° to 10° C., 18.4 percent by weight at 10° to 70° C., 16.8 percent by weight at 70° to 95° C. and 8.41 percent by weight at 95° to 125° C. according to cross fractionation chromatograph was employed for preparing a film for a first-aid sticking plaster similarly to Example 1, and a first-aid sticking plaster was prepared from this film to be subjected to measurement of physical properties of the film and evaluation of the sticking plaster. Table 1 shows the results.

Comparative Example 1

Polypropylene resin (by Himont Inc.) having a weight average molecular weight of 200,000 and elution quantities of 2.5 percent by weight at 0° to 10° C., 16.2 percent by weight at 10 to 70° C., 80.5 percent by weight at 70° to 95° C. and 0.8 percent by weight at 95° to 125° C. according to cross fractionation chromatograph was employed for preparing a film for a first-aid sticking plaster similarly to Example 1, and a first-aid sticking plaster was prepared from this film to be subjected to measurement of physical properties of the film and evaluation of the sticking plaster. Table 1 shows the results.

Comparative Example 2

An ethylene-vinyl acetate copolymer ("V505"by Mitsubishi Petrochemical Co., Ltd.) having a weight average molecular weight of 100,000 and elution quantities of 19.8 percent by weight at 0° to 10° C., 80.2 percent by weight at 10° to 70° C., 0 percent by weight at 70° to 95° C. and 0 percent by weight at 95° to 125° C. according to cross fractionation chromatograph was employed for preparing a film for a first-aid sticking plaster similarly to Example 1, and a first-aid sticking plaster was prepared from this film to be subjected to measurement of physical properties of the film and evaluation of the sticking plaster. Table 1 shows the results.

Comparative Example 3

A mixture containing 50 parts by weight of an ethylene-vinyl acetate copolymer ("EVA20F" by Mitsubishi Petrochemical Co., Ltd.) and 50 parts by weight of ethylene-propylene rubber ("TAFMER P-0280" by Mitsui Petrochemical Industries, Ltd.) was employed for preparing a film for a first-aid sticking plaster similarly to Example 1, and a first-aid sticking plaster was prepared from this film to be subjected to measurement of physical properties of the film and evaluation of the sticking plaster. Table 1 shows the weight average molecular weight of this film and elution quantities at respective temperatures according to cross fractionation chromatograph with results of the physical properties of the film and evaluation of the sticking plaster.

TABLE 1

| | Weight Average Molecular Weight | Resin Elution Quantity according to CFC (wt. %) | | | | Direction | Tensile Strength of Film (g/20 mm) | | Extention Recovery Factor (%) | Stress Residual Rate (%) | | Application Feeling of First-Aid Sticking Plaster |
|---|---|---|---|---|---|---|---|---|---|---|---|---|
| | | 0~10 °C. | 10~70 °C. | 70~95 °C. | 95~125 °C. | | in 5% Extension | in 10% Extension | | After 5 sec. | After 60 sec. | |
| Example 1 | 200,000 | 68.9 | 10.9 | 1.33 | 18.9 | MD | 216 | 310 | 88 | 74 | 58 | ◯ No |
| | | | | | | TD | 120 | 183 | 86 | 70 | 43 | Compression |
| Example 2 | 250,000 | 56.4 | 18.2 | 16.8 | 8.41 | MD | 392 | 553 | 83 | 80 | 66 | ◯ No |
| | | | | | | TD | 287 | 427 | 84 | 79 | 64 | Compression |
| Comparative Example 1 | 200,000 | 2.5 | 16.2 | 80.5 | 0.8 | MD | 750 | 980 | 55 | 96 | 89 | X Too Tight |
| | | | | | | TD | 620 | 810 | 54 | 96 | 88 | X Loosened |
| Comparative Example 2 | 100,000 | 19.8 | 80.2 | 0 | 0 | MD | 141 | 284 | 50 | 95 | 87 | X Too Tight |
| | | | | | | TD | 158 | 291 | 48 | 95 | 86 | X Loosened |
| Comparative Example 3 | 200,000 | 56.2 | 43.8 | 0 | 0 | MD | 153 | 267 | 65 | 93 | 84 | X Too Tight |
| | | | | | | TD | 158 | 261 | 63 | 94 | 84 | |

MD: Machine Direction
TD: Transverse Direction
CFC: Cross Fractionation Chromatograph

EXAMPLE 3

Polypropylene resin having a fusion peak of 165.0° C. measured by a DSC with a quantity of fusion heat of 26.3 mJ/mg and containing 15 percent by weight of a propylene-ethylene copolymer and 85 percent by weight of an ethylene-propylene copolymer (with an ethylene content of 20 percent by weight) was employed for preparing for a first-aid sticking plaster similarly to Example 1.

The film was 70 μm in thickness, and subjected to measurement of tensile strength values, extension recovery factors and stress relaxation values in the machine direction (MD) and the transverse direction (TD). Further, a first-aid sticking plaster was prepared using the film and the plaster was evaluated. Table 2 shows the results.

EXAMPLES 4 AND 5

Polypropylene resin materials having fusion peaks, quantities of fusion heat and copolymer components shown in Table 2 were employed For forming films similarly to Example 3, which were subjected to evaluation of respective properties.

EXAMPLE 6

Polypropylene resin having a fusion peak, a quantity of fusion heat and copolymer components shown in Table 2 was employed with addition of 10 percent by weight of ethylene-propylene rubber ("EP941P" by Japan Synthetic Rubber Co., Ltd.) for forming a film similarly to Example 3, which was subjected to evaluation of respective properties.

EXAMPLE 7

An intermediate layer was prepared by resin similar to that employed in Example 1, and resin employed in Example 2 was stacked on either side thereof for preparing a film of 65 μm in thickness. In preparation of this film, the resin for each surface layer and that for the intermediate layer were co-extruded by extruders of 50 mm and 65 mm in diameter respectively at extrusion temperatures of 230° C. and die temperatures of 230° C. A three-layer extrusion apparatus having a feed block, a die and three extruders was employed.

The layers were at thickness ratios of 1:10:1.

The film as obtained was subjected to evaluation similarly to Example 3. Table 2 shows the results.

Comparative Examples 4 to 6

Resin materials having characteristics shown in Table 2 were employed for forming films of 70 μm in thickness similarly to Example 3, which in turn were subjected to evaluation. Table 2 shows the results.

The weight average molecular weight of the resins used in the Examples 3 to 6 and Comparative Examples 4 to 6, which were measured by the cross fractionation chromatograph, are as follows;

|  | M.W. | CFC (weight %) | | | |
| --- | --- | --- | --- | --- | --- |
|  |  | 0–10 °C. | 10–70 °C. | 70–95 °C. | 95–125 °C. |
| Example 3 | $2.71 \times 10^5$ | 51.4 | 31.6 | 2.2 | 14.8 |
| Example 4 | $4.1 \times 10^5$ | 52.0 | 22.4 | 11.8 | 13.8 |
| Example 5 | $2.2 \times 10^5$ | 67.5 | 10.8 | 3.2 | 18.5 |
| Example 6 | $2.8 \times 10^5$ | 48.0 | 32.3 | 5.2 | 14.5 |
| Comparative Example 4 | $2.7 \times 10^5$ | 40.3 | 19.2 | 10.2 | 30.3 |
| Comparative Example 5 | $2.9 \times 10^5$ | 2.6 | 13.7 | 80.2 | 4.1 |
| Comparative Example 6 | $1.4 \times 10^5$ | 100 | 0 | 0 | 0 |

M.W. ... Weight Average Molucular Weight
CFC ... Cross Fractionation Chromatograph

TABLE 2

| | DSC Measurement | | Copolymer | | | Component B | Tensile | | | Stress Residual Rate (%) | | Application Feeling of Sticking Plaster |
| --- | --- | --- | --- | --- | --- | --- | --- | --- | --- | --- | --- | --- |
| | Fusion Peak (°C.) | Quantity of Fusion Heat/ (mJ/mg) | Component A Component Quantity (wt %) | Component Quantity (wt %) | Ethylene Content (wt %) | Additive or Content to Copolymer | Strength of Film (g/20 mm) in 5% Extension | in 10% Extension | Extension Recovery Factor (%) | After 5 sec. | After 60 sec | |
| Example 3 | 165.0 | 26.3 | Propylene-ethylene 15 | Ethylene-propylene 85 | 22 | None | TD 260 MD 280 | TD 304 MD 350 | TD 87 MD 86.5 | 74 73 | 66 63 | ○ No Compression |
| Example 4 | 142.2 | 19.8 | 30 | Ethylene-propylene 70 | 25 | None | TD 315 MD 350 | TD 402 MD 490 | TD 89.5 MD 88.8 | 71 72 | 65 63 | ○ No Compression |
| Example 5 | 159.6 | 16.7 | 20 | 80 | 25 | None | TD 208 MD 233 | TD 253 MD 334 | TD 87.0 MD 85.5 | 82 83 | 67 66 | ○ No Compression |
| Example 6 | 155.6 | 10.3 | 20 | Ethylene-propylene 80 | 30 | (1) | TD 230 MD 239 | TD 320 MD 343 | TD 87.0 MD 85.2 | 83 82 | 72 72 | ○ No Compression |
| Example 7 | | | Intermediate layer: resin of Example 1 Outer layers: resin of Example 2 | | | | TD 282 MD 310 | TD 450 MD 570 | TD 82 MD 80.5 | 48 45 | 41 39 | ○ No Compression |
| Comparative Example 4 | 161.8 | 37.0 | 55 | Ethylene-propylene 45 | 40 | None | TD 765 MD 770 | TD 863 MD 880 | TD 97 MD 97 | 95 96 | 77 79 | X Too Tight |
| Comparative Example 5 | 134.6 | 63.3 | Propylene-ethylene-butene 90 | Ethylene-propylene 10 | 20 | None | TD 1052 MD 1110 | TD 1230 MD 1310 | TD 49.6 MD 45.3 | 98 97 | 95 95 | X Too Tight |
| Comparative Example 6 | No Peak | — | Single-stage polymeri- | Ethylene-propylene | 38 | None | TD 245 MD 262 | TD 251 MD 284 | TD 96.0 MD 95.0 | 95 95 | 88 87 | X Too Tight |

TABLE 2-continued

| | DSC Measurement | | Copolymer | | Component B | Tensile | | | | | |
|---|---|---|---|---|---|---|---|---|---|---|---|
| | Fusion Peak (°C.) | Quantity of Fusion Heat/ (mJ/mg) | Component A Component Quantity (wt %) | Component Quantity (wt %) | Ethylene Content (wt %) | Additive or Content to Copolymer | Strength of Film (g/20 mm) in 5% Extension | in 10% Extension | Extension Recovery Factor (%) | Stress Residual Rate (%) After 5 sec. | After 60 sec | Application Feeling of Sticking Plaster |
| Example 6 | | | zation | 100 | | | | | | | | |

(1): ethylene-propylene copolymer 10 wt % iEXAMPLEExample 8

The polypropylene resin employed in Example 1 was employed as a first layer of 40 μm in thickness, and ethylene-propylene rubber ("TAFMER P-0280" by Mitsui Petrochemical Industries, Ltd.) was employed as a second layer of 25 μm in thickness, and extruded by a double T-die in place of the T-die 6 shown in FIG. 1 at a die temperature of about 200° C., thereby obtaining a film for a first-aid sticking plaster similarly to Example 1. The film base material was 65 μm in thickness. The film thus obtained was subjected to measurement of tensile strength in extension and stress relaxation. Table 3 shows the results.

Further, a roll-shaped original tape for a sticking plaster was cut into a width of 19 mm with a slitter similarly to Example 1, and wound up as a long tape of 200 m in length. The original tape for a sticking plaster of 19 mm in width as obtained was worked by the apparatus shown in FIG. 3, to obtain a first-aid sticking plaster.

The first-aid sticking plaster was separated from a surface-lubricated paper and applied to a forefinger, to be subjected to evaluation of application feeling and applicability. Table 3 shows the results.

EXAMPLE 9

A film for a first-aid sticking plaster and a first-aid sticking plaster were prepared similarly to Example 8, except that the polypropylene resin employed in Example 2 was employed as a first layer of 40 μm in thickness, and styrene-isoprene-styrene ("CARIFLEX TR1107P" by Shell Kagaku K.K.) was employed as a second layer of 25 μm in thickness, and subjected to evaluation of tensile strength, stress relaxation, application feeling and applicability similarly to Example 8. Table 3 shows the results.

EXAMPLE 10

A film for a first-aid sticking plaster and a first-aid sticking plaster were prepared similarly to Example 8, except that the polypropylene resin employed in Example 8 was employed as a second layer of 45 μm in thickness, and styrene-isoprene-styrene rubber ("CARIFLEX TR1107P" by Shell Kagaku K.K.) was employed as first and third layers of 10 μm in thickness, and subjected to evaluation of tensile strength, stress relaxation, application feeling and applicability similarly to Example 8. Table 3 shows the results.

EXAMPLE 11

A film for a first-aid sticking plaster and a first-aid sticking plaster were prepared similarly to Example 8, except that the polypropylene resin employed in Example 2 was employed as a second layer of 45 μm in thickness and ethylene-propylene rubber ("TAFMER P-0280" by Mitsui Petrochemical Industries, Ltd.) was employed as first and third layers of 10 μm in thickness, and subjected to evaluation of tensile strength, stress relaxation, application feeling and applicability similarly to Example 8. Table 3 shows the results.

EXAMPLE 12

A film for a first-aid sticking plaster and a first-aid sticking plaster were prepared similarly to Example 1, except that the polypropylene resin employed in Example 2 was employed as a second layer of 45 μm in thickness, styrene-isoprene-styrene rubber ("CARIFLEX TR1107P" by Shell Kagaku K.K.) was employed as a first layer of 10 μm in thickness and ethylene-propylene rubber ("TAFMER P-0280" by Mitsui Petrochemical Industries, Ltd.) was employed as a third layer of 10 μm in thickness, and subjected to evaluation of tensile strength, stress relaxation, application feeling and applicability similarly to Example 8. Table 3 shows the results.

EXAMPLE 13

A film for a first-aid sticking plaster and a first-aid sticking plaster were prepared similarly to Example 8, except that the polypropylene resin employed in Example 2 was employed as first and third layers of 25 μm in thickness, and ethylene-propylene rubber ("TAFMER P-0280" by Mitsui Petrochemical Industries, Ltd.) was employed as a second layer of 15 μm in thickness, and subjected to evaluation of tensile strength, stress relaxation, application feeling and applicability similarly to Example 8. Table 3 shows the results.

EXAMPLE 14

A film for a first-aid sticking plaster and a first-aid sticking plaster were prepared similarly to Example 8, except that the polypropylene resin employed in Example 2 was employed as first and third layers of 25 μm in thickness and styrene-isoprene-styrene rubber ("CARIFLEX TR1107P" by Shell Kagaku K.K.) was employed as a second layer of 15 μm in thickness, and subjected to evaluation of tensile strength, stress relaxation, application feeling and applicability similarly to Example 8. Table 3 shows the results.

EXAMPLE 15

A film for a first-aid sticking plaster and a first-aid sticking plaster were prepared similarly to Example 8, except that the polypropylene resin employed in Example 1 was employed as a second layer of 45 μm in thickness, and the polypropylene resin employed in Example 2 was employed used as elastomer, namely was as first and third layers of 10 μm in thickness, and subjected to evaluation of tensile strength, stress relaxation, application feeling and applicability similarly to Example 8. Table 3 shows the results.

EXAMPLE 16

A film for a first-aid sticking plaster and a first-aid sticking plaster were prepared similarly to Example 8, except that the polypropylene resin employed in Example 1 was employed as a first layer of 45 μm in thickness, and the polypropylene resin employed in Example 2 was employed as a second layer of 20 μm in thickness, and subjected to evaluation of tensile strength, stress relaxation, application feeling and applicability similarly to Example 8. Table 3 shows the results.

Comparative Example 7

A film for a first-aid sticking plaster and a first-aid sticking plaster were prepared similarly to Example 8, except that polypropylene resin used in Comparative Example 2 was employed as a first layer of 40 μm in thickness, and subjected to evaluation of tensile strength, stress relaxation, application feeling and applicability similarly to Example 8. Table 3 shows the results.

Comparative Example 8

A film for a first-aid sticking plaster and a first-aid sticking plaster were prepared similarly to Example 8, except that an ethylene-vinyl acetate copolymer ("V505" by Mitsubishi Petrochemical Co., Ltd.) used in Comparative Example 2 was employed as a first layer of 40 μm in thickness, and subjected to evaluation of tensile strength, stress relaxation, application feeling and applicability similarly to Example 8. Table 3 shows the results.

Comparative Example 9

A film for a first-aid sticking plaster and a first-aid sticking plaster were prepared similarly to Example 8, except that a mixture of 50 parts by weight of an ethylene-vinyl acetate copolymer ("EVA20F" by Mitsubishi Petrochemical Co., Ltd.) and 50 parts by weight of ethylene-propylene rubber ("TAFMER P-0280" by Mitsui Petrochemical Industries, Ltd.) was employed, and subjected to evaluation of tensile strength, stress relaxation, application feeling and applicability similarly to Example 8. Table 3 shows the results. This film had a weight average molecular weight of 200,000 and elution quantities of 56.2 percent by weight in a range of at least 0° C. and not more than 10° C., 43.8 percent by weight in a range of at least 10° C. and not more than 70° C., 0 percent by weight in a range of at least 70° C. and not more than 95° C. and 0 percent by weight in a range of at least 95° C. and not more than 125° C. according to cross fractionation chromatograph.

Comparative Example 10

A film for a first-aid sticking plaster and a first-aid sticking plaster were prepared similarly to Example 8, except that an ethylene-vinyl acetate copolymer ("EVA20F" by Mitsubishi Petrochemical Co., Ltd.) was employed as a first layer of 35 μm in thickness, and ethylene-propylene rubber ("TAFMER P-0280" by Mitsui Petrochemical Industries, Ltd.) was employed as a second layer of 35 μm in thickness, and subjected to evaluation of tensile strength, stress relaxation, application feeling and applicability similarly to Example 8. Table 3 shows the results. This film had a weight average molecular weight of 200,000 and elution quantities of 56.2 percent by weight in a range of at least 0° C. and not more than 10° C., 43.8 percent by weight in a range of at least 10° C. and not more than 70° C., 0 percent by weight in a range of at least 70° C. and not more than 95° C. and 0 percent by weight in a range of at least 95° C. and not more than 125° C. according to cross fractionation chromatograph.

TABLE 3

| | Tensile Strength in Extension (kg/19 mm) | | Stress Residual Rate (%) | | Application Feeling of First-Aid Sticking Plaster | Applicability of First-Aid Sticking Plaster |
| --- | --- | --- | --- | --- | --- | --- |
| | 5% | 10% | 5 sec. | 60 sec. | | |
| Example 8 | 0.150 | 0.202 | 77 | 57 | ○ No Compression | ○ Easy to Apply ○ No Crease |
| Example 9 | 0.216 | 0.346 | 80 | 57 | ○ No Compression | ○ Easy to Apply ○ No Crease |
| Example 10 | 0.170 | 0.281 | 80 | 57 | ○ No Compression | ○ Easy to Apply ○ No Crease |
| Example 11 | 0.214 | 0.309 | 80 | 59 | ○ No Compression | ○ Easy to Apply ○ No Crease |
| Example 12 | 0.192 | 0.295 | 80 | 58 | ○ No Compression | ○ Easy to Apply ○ No Crease |
| Example 13 | 0.247 | 0.385 | 80 | 58 | ○ No Compression | ○ Easy to Apply ○ No Crease |
| Example 14 | 0.189 | 0.301 | 80 | 57 | ○ No Compression | ○ Easy to Apply ○ No Crease |
| Example 15 | 0.295 | 0.394 | 69 | 49 | ○ No Compression | ○ Easy to Apply ○ No Crease |
| Example 16 | 0.297 | 0.396 | 69 | 49 | ○ No Compression | ○ Easy to Apply ○ No Crease |
| Comparative Example 7 | 0.713 | 0.931 | 96 | 89 | X (1) | X Too Hard ○ No Crease |
| Comparative Example 8 | 0.140 | 0.281 | 95 | 87 | X Too Tight X Loosened | ○ Easy to Apply ○ No Crease |
| Comparative Example 9 | 0.153 | 0.287 | 93 | 84 | X Too Tight X Loosened | ○ Easy to Apply ○ No Crease |
| Comparative Example 10 | 0.153 | 0.267 | 93 | 84 | X Too Tight X Loosened | ○ Easy to Apply ○ No Crease |

(1): Inferior Stretching Follow Up, Too Tight

EXAMPLE 17

100 parts by weight of polypropylene resin employed in Example 1 and 50 parts by weight of polypropylene resin employed in Example 2 were employed to prepare a film for a first-aid sticking plaster and a first-aid sticking plaster similarly to Example 8, and subjected to measurement of tensile strength in extension and stress relaxation of the film and evaluation of application feeling and applicability of the sticking plaster to a human body portion. Table 4 shows the results.

EXAMPLE 18

A film for a first-aid sticking plaster and a first-aid sticking plaster were prepared similarly to Example 17 except that the film was 80 μm in thickness, and subjected to evaluation of tensile strength, stress relaxation, application feeling and applicability similarly to Example 17. Table 4 shows the results.

EXAMPLE 19

A film for a first-aid sticking plaster and a first-aid sticking plaster were prepared similarly to Example 17 except that 100 parts by weight of polypropylene resin employed in Example 2 and 50 parts by weight of ethylene-propylene rubber ("TAFMER P-0280" by Mitsui Petrochemical Industries, Ltd.) were employed, and subjected to evaluation of tensile strength, stress relaxation, application feeling and applicability similarly to Example 17. Table 4 shows tile results.

EXAMPLE 20

A film for a first-aid sticking plaster and a first-aid sticking plaster were prepared similarly to Example 17 except that 100 parts by weight of polypropylene resin employed in Example 2 and 20 parts by weight of styrene-isoprene-styrene rubber ("CARIFLEX TR1107P" by Shell Kagaku K.K.) were employed, and subjected to evaluation of tensile strength, stress relaxation, application feeling and applicability similarly to Example 17. Table 4 shows the results.

EXAMPLE 21

A film for a first-aid sticking plaster and a first-aid sticking plaster were prepared similarly to Example 17 except that the film was 100 μm in thickness, and subjected to evaluation Of tensile strength, stress relaxation, application feeling and applicability similarly to Example 17. Table 4 shows the results.

Comparative Example 11

A film for a first-aid sticking plaster and a first-aid sticking plaster were prepared similarly to Example 17 except that the film was 25 μm in thickness, and subjected to evaluation of tensile strength, stress relaxation, application feeling and applicability similarly to Example 17. Table 4 shows the results.

Comparative Example 12

A Film for a first-aid sticking plaster and a first-aid sticking plaster were prepared similarly to Example 17 except that the film was 210 μm in thickness, and subjected to evaluation of tensile strength, stress relaxation, application feeling and applicability similarly to Example 17. Table 4 shows the results.

Comparative Example 13

A film for a first-aid sticking plaster and a first-aid sticking plaster were prepared similarly to Example 17 except that an ethylene-vinyl acetate copolymer ("V505" by Mitsubishi Petrochemical Co., Ltd.) was employed as thermoplastic resin, and subjected to evaluation of tensile strength, stress relaxation, application feeling and applicability similarly to Example 17. Table 4 shows the results.

Comparative Example 14

A film for a first-aid sticking plaster and a first-aid sticking plaster were prepared similarly to Example 17 except that 50 parts by weight of an ethylene-vinyl acetate copolymer ("EVA20F" by Mitsubishi Petrochemical Co., Ltd.,) and 50 parts by weight of ethylene-propylene rubber ("TAFMER P-0280"by Mitsui Petrochemical Industries, Ltd.) were employed as thermoplastic resin materials, and subjected to evaluation of tensile strength, stress relaxation, application feeling and applicability similarly to Example 17. Table 4 shows the results.

Comparative Example 15

A film for a first-aid sticking plaster and a first-aid sticking plaster were prepared similarly to Example 17 except that ethylene-propylene rubber ("TAFMER P-0280" by Mitsui Petrochemical Industries, Ltd.) was employed as thermoplastic resin, and subjected to evaluation of tensile strength, stress relaxation, application feeling and applicability similarly to Example 17. Table 4 shows the results.

Comparative Example 16

A film for a first-aid sticking plaster and a first-aid sticking plaster were prepared similarly to Example 17 except that polypropylene resin employed in Comparative Example 1 was employed as thermoplastic resin, and subjected to evaluation of tensile strength, stress relaxation, application feeling and applicability similarly to Example 17. Table 4 shows the results.

TABLE 4

|  | Tensile Strength in Extension (kg/19 mm) | | | Stress Residual Rate (%) | | Application Feeling of First-Aid Sticking Plaster | Applicability of First-Aid Sticking Plaster |
| --- | --- | --- | --- | --- | --- | --- | --- |
|  | 5% | 10% | 30% | 5 sec | 300 sec |  |  |
| Example 17 | 0.213 | 0.303 | 0.432 | 75 | 49 | ○ No Compression * A | ○ Easy to Apply ○ No Crease |
| Example 18 | 0.262 | 0.373 | 0.532 | 75 | 49 | ○ No Compression * A | ○ Easy to Apply ○ No Crease |
| Example 19 | 0.218 | 0.328 | 0.405 | 80 | 60 | ○ No Compression * A | ○ Easy to Apply ○ No Crease |

TABLE 4-continued

| | Tensile Strength in Extension (kg/19 mm) | | | Stress Residual Rate (%) | | Application Feeling of First-Aid Sticking Plaster | Applicability of First-Aid Sticking Plaster |
|---|---|---|---|---|---|---|---|
| | 5% | 10% | 30% | 5 sec | 300 sec | | |
| Example 20 | 0.205 | 0.301 | 0.401 | 79 | 55 | ○ No Compression * A | ○ Easy to Apply ○ No Crease |
| Example 21 | 0.328 | 0.466 | 0.665 | 76 | 50 | ○ No Compression * A | ○ Easy to Apply ○ No Crease |
| Comparative Example 11 | 0.082 | 0.126 | 0.189 | 74 | 48 | ○ No Compression X Loosened | X Easy to Crease |
| Comparative Example 12 | 0.262 | 0.976 | 1.267 | 77 | 51 | ○ No Compression * B | X Too Tight ○ No Crease |
| Comparative Example 13 | 0.262 | 0.284 | 0.413 | 95 | 87 | X Too Tight X Loosened | ○ Easy to Apply ○ No Crease |
| Comparative Example 14 | 0.153 | 0.267 | 0.387 | 93 | 84 | X Too Tight X Loosened | ○ Easy to Apply ○ No Crease |
| Comparative Example 15 | 0.057 | 0.118 | 0.175 | 95 | 77 | X Too Tight X Loosened | X (1) |
| Comparative Example 16 | 0.765 | 0.863 | 0.821 | 71 | 44 | ○ No Compression * B | X Too Hard ○ No Crease |

(1): Extended too much, Easy to Crease
* A: Superior Stretching Follow Up
* B: Inferior Stretching Follow Up

EXAMPLE 22

The polypropylene resin employed in Example 2 was extruded similarly to Example 1, at a die temperature of about 240° C. Then, the film as obtained was transversely uniaxially oriented by a tenter drawer at a drawing temperature of 100° C. and an annealing temperature of 120° C. for an annealing time of 3 minutes at a drawing magnification of 1.5 times. Then, a film for a first-aid sticking plaster was obtained similarly to Example 1. The film was 65 μm in thickness. The film was subjected to measurement of tensile strength, stress relaxation and heat contraction in extension in a transverse (drawing) direction. Table 5 shows the results.

First-aid sticking plasters were thereafter obtained similarly to Example 1 .and subjected to evaluation.

EXAMPLE 23

A film for a first-aid sticking plaster and a first-aid sticking plaster were prepared similarly to Example 22 except that the polypropylene resin employed in Example 2 was subjected to transverse uniaxial tenter orientation at a drawing temperature of 120° C. and an annealing temperature of 140° C. for an annealing time of 3 minutes at a drawing magnification of 3.0 times, and subjected to evaluation of tensile strength, stress relaxation, application feeling and applicability similarly to Example 22. Table 5 shows the results.

EXAMPLE 24

A film for a first-aid sticking plaster and a first-aid sticking plaster were prepared similarly to Example 22 except that the polypropylene resin employed in Example 2 was subjected to longitudinal streching at a drawing temperature of 100° C. and an annealing temperature of 120° C. for an annealing time of 3 minutes at a drawing magnification of 1.5 times. A roll-shaped original tape was slit into a width of 19 mm, and punched in a machine direction MD, i.e., a drawing direction. The film and the first-aid sticking plaster were subjected to evaluation of tensile strength, stress relaxation, application feeling and applicability similarly to Example 22. Table 5 shows the results.

EXAMPLE 25

A first-aid sticking plaster was prepared similarly to Example 21 except that polypropylene resin employed in Example 2 was employed as a second layer of 45 μm in thickness, and ethylene-propylene rubber ("TAFMER P-0280" by Mitsui Petrochemical Industries, Ltd. ) was employed as first and third layers of 10 μm in thickness and extruded by a double T-die at a die temperature of about 200° C. for forming a film, which in turn was extremely drawn in a transverse direction by a tenter drawer at a drawing temperature of 100° C. and an annealing temperature of 120° C. for an annealing time of 3 minutes at a drawing magnification of 1.5 times, and subjected to evaluation similarly to Example 22. Table 5 shows the results.

EXAMPLE 26

A film for a first-aid sticking plaster and a first-aid sticking plaster were prepared and evaluated similarly to Example 25, except that the polypropylene resin employed in Example 1 was employed as a first layer of 45 μm, and the polypropylene resin employed in Example 2 for the second layer was employed as a second layer of 20 μm in thickness. Table 5 shows the results.

Comparative Example 17

A film for a first-aid sticking plaster and a first-aid sticking plaster were prepared similarly to Example 22 except that the polypropylene resin employed in Example 2 was subjected to transverse uniaxial tenter orientation at a drawing temperature of 60° C. and an annealing temperature of 120° C. for an annealing time of 3 minutes at a drawing magnification of 1.5 times, and subjected to evaluation of tensile strength, stress relaxation, application feeling and applicability similarly to Example 22. Table 5 shows the results.

Comparative Example 18

A film for a first-aid sticking plaster and a first-aid sticking plaster were prepared similarly to Example 22 except that the polypropylene resin employed in Example 2 was subjected to transverse uniaxial tenter orientation at a drawing temperature of 160° C. and an annealing temperature of 160° C. for an annealing time of 3 minutes at a drawing magnification of 1.5 times, and subjected to evaluation of tensile strength, stress relaxation, application feeling and applicability similarly to Example 22. Table 5 shows the results.

Comparative Example 19

A film for a first-aid sticking plaster and a first-aid sticking plaster were prepared similarly to Example 22 except that the polypropylene resin employed in Example 2 was subjected to transverse uniaxial tenter orientation at a drawing temperature of 120° C. and an annealing temperature of 140° C. for an annealing time of 3 minutes at a drawing magnification of 5.0 times, and subjected to evaluation of tensile strength, stress relaxation, application feeling and applicability similarly to Example 22. Table 5 shows the results.

TABLE 5

| | Extension Temperature (°C.) | Annealing Temperature (°C.) | Extention Magnification (times) | Tensile Strength in Extension (g/20 mm) | | | Stress Residual Rate (%) | | Heat Contraction (%) | Remarks |
|---|---|---|---|---|---|---|---|---|---|---|
| | | | | 5% | 10% | 50% | After 5 sec. | After 60 sec. | | |
| Example 22 | 100 | 120 | 1.5 | 222 | 364 | 806 | 78 | 58 | 0.9 | Flexibility ○ |
| Example 23 | 120 | 140 | 3.0 | 251 | 395 | 813 | 72 | 55 | 0.9 | Flexibility ○ |
| Example 24 | 100 | 120 | 1.5 | 221 | 381 | 858 | 79 | 60 | 1.0 | (1) |
| Example 25 | 100 | 120 | 1.5 | 225 | 374 | 836 | 80 | 69 | 0.9 | Flexibility ○ |
| Example 26 | 100 | 120 | 1.5 | 312 | 491 | 1008 | 69 | 59 | 0.9 | Flexibility ○ |
| Comparative Example 17 | 60 | 120 | 1.5 | 257 | 393 | 907 | 77 | 57 | 5.2 | Heat Contraction irregularity X |
| Comparative Example 18 | 160 | 160 | 1.5 | 273 | 391 | 421 | 69 | 55 | 0.6 | 50% Tensile Strength X |
| Comparative Example 19 | 120 | 140 | 1.5 | 229 | 434 | 880 | 82 | 69 | 6.6 | Heat Contraction X |

(1): Vertical Uniaxial Proximity Orientation

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A film for a first-aid sticking plaster, consisting of polypropylene resin having a weight average molecular weight within a range of 80,000 to 500,000, with resin elution quantities being within ranges of 45 to 80 percent by weight at 0° to 10° C., 5 to 35 percent by weight at 10° to 70° C., 1 to 30 percent by weight at 70° to 95° C., and 5 to 35 percent by weight at 95° to 125° C. in the total polypropylene resin quantity according to cross fractionation chromatograph.

2. A film for a first-aid sticking plaster in accordance with claim 1, wherein at least one fusion peak of said polypropylene resin being measured by a differential scanning calorimeter exists between 130° C. and 170° C., a total quantity of fusion heat being 5 to 40 mJ/mg at said peak.

3. A film for a first-aid sticking plaster in accordance with claim 1, being obtained by multistage polymerization of polymerizing 5 to 55 percent by weight of at least one material selected from a group of a propylene homopolymer, an ethylene-propylene copolymer and a propylene-α-olefin copolymer in a first stage, and polymerizing 65 to 95 percent by weight of an ethylene-propylene copolymerized elastomer in a second or subsequent stage.

4. A film for a first-aid sticking plaster in accordance with claim 3, wherein said ethylene-propylene copolymerized elastomer contains ethylene component in a range of 15 to 65 percent by weight.

5. A film for a first-aid sticking plaster in accordance with claim 1, having not a clear yield point, with stress residual rates of not more than 80% and 60% after lapses of 5 and 300 seconds respectively in extension by 10%.

6. A film for a first-aid sticking plaster in accordance with claim 5, wherein relations of $F(30)>F(10)>F(5)$ and $0.2 \text{ kgf} < F(30) \leq 1.2 \text{ kgf}$, $0.2 \text{ kgf} \leq F(10) \leq 0.8 \text{ kgf}$, and $0.1 \text{ kgf} \leq F(5) \leq 0.6 \text{ kgf}$ hold assuming that $F(x)$ represents tensile strength of a film having a width of 19 mm in extension by x %.

7. A film for a first-aid sticking plaster in accordance with claim 1, wherein a layer consisting of at least either olefin thermoplastic elastomer or a styrene thermoplastic elastomer is stacked on said polypropylene resin layer.

8. A film for a first-aid sticking plaster in accordance with claim 1, being drawn at least in a single direction at a drawing temperature of 75° C. to 150° C. so that drawing magnification is 1.1 to 4 times.

9. A film for a first-aid sticking plaster in accordance with claim 8, being further annealed in a temperature range of 80° to 160° C. after said drawing.

10. A film for a first-aid sticking plaster in accordance with claim 2, wherein a layer consisting of at least either an olefin thermoplastic elastomer or a styrene thermoplastic elastomer is stacked on said polypropylene resin layer.

11. A film for a first-aid sticking plaster in accordance with claim 3, wherein a layer consisting of at least either an olefin thermoplastic elastomer or a styrene thermoplastic elastomer is stacked on said polypropylene resin layer.

12. A film for a first-aid sticking plaster in accordance with claim 4, wherein a layer consisting of at least either an olefin thermoplastic elastomer or a styrene thermoplastic elastomer is stacked on said polypropylene resin layer.

13. A film for a first-aid sticking plaster in accordance with claim 5, wherein a layer consisting of at least either an olefin thermoplastic elastomer or a styrene thermoplastic elastomer is stacked on said polypropylene resin layer.

14. A film for a first-aid sticking plaster in accordance with claim 6, wherein a layer consisting of at least either an olefin thermoplastic elastomer or a styrene thermoplastic elastomer is stacked on said polypropylene resin layer.

15. A film for a first-aid sticking plaster in accordance with claim 2, being drawn at least in a single direction at a drawing temperature of 75° C. to 150° C. so that a drawing magnification is 1.1 to 4 times.

16. A film for a first-aid sticking plaster in accordance with claim 3, being drawn at least in a single direction at a drawing temperature of 75° C. to 150° C. so that a drawing magnification is 1.1 to 4 times.

17. A film for a first-aid sticking plaster in accordance with claim 4, being drawn at least in a single direction at a drawing temperature of 75° C. to 150° C. so that a drawing magnification is 1.1 to 4 times.

18. A film for a first-aid sticking plaster in accordance with claim 5, being drawn at least in a single direction at a drawing temperature of 75° C. to 150° C. so that a drawing magnification is 1.1 to 4 times.

19. A film for a first-aid sticking plaster in accordance with claim 6, being drawn at least in a single direction at a drawing temperature of 75° C. to 150° C. so that a drawing magnification is 1.1 to 4 times.

20. A film for a first-aid sticking plaster in accordance with claim 7, being drawn at least in a single direction at a drawing temperature of 75° C. to 150° C. so that a drawing magnification is 1.1 to 4 times.

* * * * *